(12) United States Patent
Muller et al.

(10) Patent No.: US 6,485,300 B1
(45) Date of Patent: Nov. 26, 2002

(54) TOOTHBRUSH WITH FLUORESCENCE MEANS FOR LOCATING DENTAL PLAQUE

(75) Inventors: Werner Muller, Wetzlar-Nauborn (DE); Michael Schopplein, Wetzlar-Nauborn (DE)

(73) Assignee: Helmut Hund GmbH, Watzlar-Nauborn (DE)

( * ) Notice: Subject to any disclaimer, the term of this patent is extended or adjusted under 35 U.S.C. 154(b) by 0 days.

(21) Appl. No.: 09/700,601

(22) PCT Filed: May 12, 1999

(86) PCT No.: PCT/EP99/03273

§ 371 (c)(1),
(2), (4) Date: Nov. 15, 2000

(87) PCT Pub. No.: WO99/59462

PCT Pub. Date: Nov. 25, 1999

(30) Foreign Application Priority Data

May 16, 1998 (GB) .............................................. 9810471

(51) Int. Cl.⁷ ................................................. A61C 1/00
(52) U.S. Cl. ...................................................... 433/29
(58) Field of Search ........................ 433/29, 215, 216; 15/167.1, 167.2; 356/317, 318

(56) References Cited

U.S. PATENT DOCUMENTS 5,590,660 A * 1/1997 MacAulay et al. ......... 128/664
6,024,562 A * 2/2000 Hibst et al. .................... 433/29
6,026,828 A * 2/2000 Altshuler ..................... 132/311
6,102,704 A * 8/2000 Eibofner et al. ............ 433/215
6,186,780 B1 * 2/2001 Hibst et al. .................... 433/29

FOREIGN PATENT DOCUMENTS

| EP | 0 56 877 A | 8/1982 |
| WO | WO 92 06671 A | 4/1992 |
| WO | WO 97 01298 | 1/1997 |

* cited by examiner

Primary Examiner—Nicholas D. Lucchesi
(74) Attorney, Agent, or Firm—Nora Stein-Fernandez

(57) ABSTRACT

An apparatus for detecting biological deposits on the surface of a tooth. The device has illumination means to direct exciting radiation onto a test tooth surface and detection means to detect fluorescence emission from the test tooth surface at a wavelength associated with that of auto fluorescence emission from clean tooth surface. The intensity of the said fluorescence emission from the test tooth surface is compared with an intensity of auto fluorescence emission from clean tooth surface and the comparison is associated with the presence of deposits on the test tooth surface. The device is preferably embodied in a toothbrush which indicates to the user that deposits are present and are being removed.

44 Claims, 9 Drawing Sheets

TOOTHBRUSH WITH FLUORESCENCE MEANS FOR LOCATING DENTAL PLAQUE

This invention relates to a novel apparatus for the detection of biological deposits, in particular deposits of plaque, on the surfaces of teeth. In particular the invention relates to apparatus for this purpose which use fluorescence measurements to detect such deposits. In particular the invention relates to apparatus for this purpose which may be incorporated in a hand- or electrically operated toothbrush.

The term "biological deposits" used herein refers generally to deposits of material of biological origin, e.g. plaque, bacteria, tartar, calculus etc. which are generally regarded as undesirable for dental hygiene. Dental plaque is a complex organic deposit generated in part by the activity of bacteria on the teeth or contamination, e.g. food deposits on the teeth, and is an undesirable precursor to tooth decay and the development of dental caries.

It is desirable to detect such deposits on the teeth before removing them, for example by toothbrushing, as detection indicates the areas at which dental cleaning effort should be concentrated. Such deposits can be difficult to detect in situ in vivo on the teeth. It is especially important to detect dental plaque. For detection of plaque it is known to use fluorescence measurement. In the state of the art there are two general methods for detecting dental plaque using fluorescence, secondary fluorescence and auto fluorescence. In secondary fluorescence teeth suspected of bearing plaque are treated with a fluorescent label material which preferentially binds to dental plaque, and after excess of the unbound material has been washed away from the teeth, the fluorescence emission, in response to illumination by exciting radiation, of the label material at areas of the tooth at which it has bound to plaque is detected to indicate the presence of dental plaque. WO 92/06671 and WO 97/01298 disclose typical methods based upon secondary fluorescence and apparatus which exploit such methods.

Auto fluorescence methods do not use a fluorescence label but instead detect the fluorescence emission from dental plaque itself in response to illumination by exciting radiation. U.S. Pat. No. 5,382,163, DE 29704185, DE 29705934, EP 0774235, and also WO 97/01298 disclose methods of this type and apparatus for performing these methods. Typically in these disclosures auto fluorescence emission by dental plaque at emission wavelengths above ca. 600 nm is detected and associated with the presence of dental plaque.

Optical methods are also known for the detection of dental caries, i.e. the tooth disease which can result from the non removal of plaque. Typical methods of this type are disclosed in for example U.S. Pat. No. 4,290,433, EP 0862897 and WO 97/42869, but these methods do not detect plaque deposits themselves.

These methods and apparatus disclosed in the state of the art for the detection of plaque have not proved to be optimum, especially when there is relatively little plaque present—a state at which tooth cleaning is best carried out to remove early deposits of plaque before they can build up. Plaque deposits have different characteristics which vary from person to person, so it is desirable to provide a system which can be "personalised". Methods which require the application of fluorescent label materials to teeth are prima facie inconvenient.

It is therefore an object of this invention to provide an apparatus and a method for detecting biological deposits on teeth in vivo, which in part at least solves the problems of the state of the art.

According to a first aspect of this invention, an apparatus for detecting biological deposits on the surface of a tooth comprises;

illumination means to direct exciting radiation onto a test tooth surface, detection means to detect fluorescence emission from the test tooth surface at a wavelength associated with that of auto fluorescence emission from a substantially biological deposit-free tooth surface, means to make a comparison of the intensity of the said fluorescence emission from the test tooth surface with an intensity of auto fluorescence emission, at a wavelength associated with that of auto fluorescence emission from a substantially biological deposit free tooth surface, from a tooth surface known to have less biological deposit thereon than is present at the test tooth surface, means to associate the comparison thus obtained with the presence of biological deposits on the test tooth surface, and, indicator means to indicate the presence of such biological deposits to a user of the apparatus.

The test tooth surface may be any tooth surface in the user's mouth which is believed or suspected to have a biological deposit such as plaque thereon, or which the user desires to test for the presence of plaque, usually with the intention of removing such deposits e.g. using a toothbrush.

For convenience a tooth surface known to have less biological deposit thereon than is present at the test tooth surface is termed hereafter a "clean" tooth surface. A clean tooth surface may have biological deposit thereon but quantitatively less than is present at the test tooth surface, or preferably is free or substantially free of biological deposit.

The apparatus of this aspect of the invention is based upon the discovery that a tooth surface which is free of biological deposit, when illuminated with exciting radiation, emits a strong and easily detectable auto fluorescence emission, generally peaking in intensity at ca. 450 nm, but having a considerable intensity at higher wavelengths, and that this auto fluorescence emission is strongly attenuated by the presence of even small quantities of biological deposits such as dental plaque on the tooth surface, so that the intensity of this auto fluorescence is reduced if biological deposits are present on the tooth surface. It has also been discovered that this characteristic auto fluorescence is relatively unaffected by other features of the tooth surface, for example the colour or natural reflectivity of the teeth whether due to natural variations, age, sex, deposits from tobacco smoking etc. so that the apparatus and the method it employs are sufficiently unaffected by variations between the teeth of individual persons using the apparatus. Also the majority of commercial toothpastes are believed to emit no fluorescence in response to illumination by radiation which causes fluorescence emission from tooth surfaces or biological deposits thereon, and to differ in their spectra from natural enamel, so are not believed to interfere with the operation of the device of this invention.

Although for the purpose of exciting fluorescence a preferred wavelength for the exciting radiation is below 420 nm, radiation of this, short wavelength may in some circumstances be harmful to dental tissues. Consequently for safety reasons the exciting radiation is preferably at a wavelength 470±40 nm. Suitable and preferred illumination means are discussed in more detail below.

A tooth surface free of biological deposits emits a fluorescence emission in the wavelength region above 420 nm, typically as shown in FIG. 1, peaking in intensity above ca. 450 nm. Therefore the detection means may detect the fluorescence emission at such wavelengths above 420 nm.

Suitably, inter alia to differentiate the exciting radiation from the fluorescence emission, the detector means detects fluorescence emission radiation at a wavelength of above 520 nm. At these wavelengths the auto fluorescence emission from the surface of teeth which are free or substantially free of biological deposits is still strong. It is preferred to measure the fluorescence emission radiation at a wavelength above ca. 530 nm, for example over the region 530–630 nm.

The means to make the comparison of the relative intensities of the auto fluorescence emission from the test tooth surface with that from a clean tooth surface may comprise an electronic signal/data processing system processing an electronic signal corresponding to the auto fluorescence emission. Preferably the system measures the area under the intensity/wavelength graph. Suitable signal/data processing systems which can do this are well known in the art.

The intensity of the auto fluorescence from a clean tooth surface may be determined in a number of ways.

In one construction of the device of this invention, the intensity of auto fluorescence emission from biological deposit-free or substantially biological deposit-free tooth surfaces may be treated as a constant for a given intensity of exciting radiation between individual persons as mentioned above. Such an intensity may be determined experimentally and may be stored as a reference standard in the apparatus as constructed and supplied to a user, e.g. in its electronics and/or software.

In an alternative construction the apparatus may be initially applied to a user's tooth surface believed to be a clean tooth surface, e.g. the crown of a tooth, or a front, e.g. incisor tooth, which generally accumulate no or relatively little biological deposits such as dental plaque. In many cases such "clean" surfaces can be considered as a substantially biological deposit-free tooth surface. The intensity of auto fluorescence emissions from a clean surface may be measured, and used as a basis for the comparison with the intensity of emission from the test tooth surface. After the apparatus has been first applied to a clean tooth surface of the user the apparatus may then subsequently is applied to the test tooth surface, and a comparison is made between the auto fluorescence measured at the clean tooth surface and at the test tooth surface.

In another alternative construction the detection means may be moveable between locations on the user's teeth, e.g. across the surfaces of the user's teeth, e.g. over a plurality or all of the user's teeth, so that in the course of this movement the exciting radiation is directed onto a plurality of tooth surfaces on the same or different teeth. These surfaces are likely to differ in the quantity of biological deposits thereon, i.e. some surfaces having relatively less biological deposits thereon, to the extent that some such surfaces are "clean" surfaces relative to the test tooth surface. For example the detection means may be moveable between regions on the base of the teeth and regions for example on the crowns of the teeth, or for example on front teeth, which as explained above are likely to be substantially free of biological deposits. This is termed a "dynamic" measurement, i.e. working by a movement of the device over the user's teeth.

As the device of the invention in this construction is moved over the teeth surfaces of the user's mouth it will encounter areas of test tooth surface where biological deposits are present, and also clean areas of the teeth. As a result the intensity of the fluorescence emission radiation detected by the detection device as it is moved around the mouth of the user over the tooth surfaces will vary between minima representing test tooth surfaces where there is a biological deposit, and maxima where there are clean tooth surfaces. Therefore the variation of fluorescence emission detected as the device moves around the user's mouth is likely to show a series of intensity peaks and/or plateaus (hereinafter collectively referred to as "peaks") with time, and these peaks will show variation between regions of test tooth surface with biological deposit and clean tooth surfaces, relatively low peaks occurring at the former and relatively high peaks occurring at the latter. The difference in height between these relatively low and high peaks is representative of the difference in the amount of biological deposits of the test tooth surfaces. With the device of this construction it may be possible to detect the presence of biological deposits on a test tooth surface of a single tooth.

Alternatively by detecting the fluorescence emission peaks over a period of time during which the device moves over several teeth or all the user's teeth, the presence of biological deposits on one or more test tooth surfaces may be detected. This can give a "whole mouth" indication of the presence of deposit, i.e. showing the presence of deposits somewhere in the user's mouth but possibly not giving a precise location on a specific tooth.

Additionally or alternatively the device may be adapted, e.g. by means of internal electronics and/or software to use pulse height analysis (a known technique) to measure the difference between highest and lowest peaks. Whilst this difference is changing, i.e. reducing, during a process of tooth cleaning e.g. brushing this indicates that deposits are present and are being removed, as more and more of the tooth surfaces become clean.

Additionally or alternatively the device may be adapted, e.g. again using pulse height analysis to measure the mean between highest and lowest peaks. Whilst this mean is increasing, as more and more of the tooth surfaces become clean, during a process of toothbrushing this indicates that deposits are present and are being removed.

There are also likely to be "false" minima of fluorescence emission where the illumination means is not directing the exciting radiation at tooth surfaces, and/or the detection means is/are not positioned to detect fluorescence emission from tooth surfaces. For example this may occur when the illumination means and/or detection means are aimed at or adjacent to gaps in the teeth, other parts of the mouth than teeth, or dental fillings etc. The device of the invention may be constructed to ignore such false minima, i.e. any fluorescence intensity peak below a specified certain value, e.g. responding only to intensity peaks within certain specified limits corresponding to the limits within which fluorescence emission from tooth surfaces is actually expected to occur.

Therefore according to this last described embodiment of the device of the invention, the detection means may be constructed to;

detect a fluorescence emission during a period of time over which the detection device moves from one tooth area to one or more other tooth areas;

detect peaks in the emission intensity with time;

and to measure and compare the heights of such peaks.

In particular in this embodiment the device may be constructed to measure the difference between the height of the lowest and the highest of such peaks, and to associate this difference with the presence of biological deposits which are then indicated to the user. For example a difference of 5–90% may occur, e.g. 5–50%. Alternatively or additionally in this embodiment the device may be constructed to measure the difference between the height of the lowest and the highest of such peaks, to then calculate the mean, and to associate an increase in this mean with the presence of biological deposits which are then indicated to the user. Typically an increase in the mean of 5–90% may occur, e.g. 5–50%.

The detection of such peaks of fluorescence emission intensity, and the measurement and comparison of the peak heights is easily within the ability of modern detection, electronic and data processing systems.

In another alternative construction the device of the invention may be provided with detection means to detect fluorescence emission from two spaced apart regions of tooth surface, and to compare the relative intensities of fluorescence emission from these two spaced apart surfaces, to associate any such difference with the presence of biological deposits on the tooth surface and indicate the presence of such deposits to the user.

If the distance the two regions are spaced apart is appropriate it will be likely that if one of the regions has biological deposit thereon the other will be a clean region. A suitable maximum spacing apart of the two regions may be up to the height, i.e. the distance from the junction with the gum (i.e. the gingival margin) to the crown of the tooth. Typically the spacing apart of these two regions may therefore be from ca. 2.0 mm up to the height of a tooth, e.g. 2–10 mm.

The device of this construction may have two detection means positioned relative to each other so that when the device is inserted into the mouth one of the two detection means is likely to be positioned adjacent a tooth at or near the gumline and the other is at or near the crown of the tooth. For example if the device of the invention comprises a toothbrush head, the two detection means may be positioned across the width (i.e. the direction perpendicular to the head-handle direction) of the toothbrush head, so that as the head is used for toothbrushing the two detection means are likely to become positioned in the manner described above.

The device according to this embodiment may have at least two detection means, at least two of which are spaced apart at the above-mentioned distances. Suitably the detection of fluorescence emission of the two spaced apart distances may be performed simultaneously. Any difference between the intensity of fluorescence emission detected at the two spaced apart regions can be associated with the presence of biological deposits. Of course the situation may occur that in use one of the spaced apart regions, e.g. one of two or more detection means is not in a position to detect fluorescence emission from a tooth surface, e.g. if it is adjacent a gap in the teeth, mouth tissue, fillings etc. In such a case the difference in intensity of the fluorescence emission detected at the spaced apart regions is likely to exceed the maximum difference that would be expected to occur between a test tooth surface with a biological deposit on it, and a clean surface, and the device may be constructed to ignore all such differences which are greater than a specified certain value, for example responding only to differences between certain specified limits.

In practice it may be found that even when the entire tooth surface is "clean" there may be differences in fluorescence emission from different areas of the teeth. In particular a gradient in fluorescence intensity along the vertical axis of the tooth may be encountered, greater intensity being observed at the cervical, or gingival margin, region near the base of the tooth than at the incisor aspect or crown of the tooth. This gradient may be affected by the presence of biological deposits such as plaque, as more deposit is expected to accumulate near the base of the tooth. Therefore the gradient may be steeper on a tooth where there are biological deposits than is the situation for a clean tooth. Consequently the device of the invention may be constructed to observe the presence of, and/or measure such a gradient as the device moves from one part of a tooth surface to another. For example the device may be constructed to detect and/or measure changes in such a gradient, e.g. a reduction of steepness of this gradient, during a process of tooth cleaning, because as biological deposits are removed from e.g. the base of the tooth the gradient of fluorescence emission intensity between the base and the crown is likely to decrease. The device may be constructed to use this for the indication of the presence of biological deposit on a test tooth surface.

The device of this last described embodiment is particularly suited to detect biological deposits on a single tooth, and may also be suitable for detecting dental deposits somewhere among a plurality of teeth or among all of the user's teeth, for example giving the user a "whole mouth" indication of the presence of biological deposits somewhere in the whole mouth of the user.

The setting up and calibration of the device of the invention, e.g. setting of the limits of fluorescence emission intensity to be detected and measured and associated with the presence of biological deposits on test tooth surfaces, setting the limits of intensity between which the device responds etc is a matter of design for any specific construction of the device of the invention. Using modern electronics and internally embedded software this may be easily achieved by means within the competence of those skilled in the art. For example the device of the invention may be set to respond to a difference of a specified percentage between fluorescence emission intensity from clean tooth surfaces and test tooth surfaces on which there is a deposit of biological deposit. For example the device may be set to respond to a difference in the range 1–90%, e.g. in the range 1–5%, or 1–10%, or 1–20%, or 30% or more between fluorescence emission intensity from clean tooth surfaces and test tooth surfaces on which there is a deposit of biological deposit.

The means to associate the comparison thus obtained with the presence of biological deposit such as dental plaque on the test tooth surface may also comprise a signal/data processing system, programed to associate a difference in the intensity of the auto fluorescence emission produced from the test tooth surface and that associated with auto fluorescence emission from a substantially biological deposit-free tooth surface with the presence of biological deposits such as plaque. This signal/data processing system may comprise an application specific integrated circuit ("ASIC") built into the device. For example the data processing system may associate any such difference with the presence of deposits such as plaque. Alternately the data processing system may be programmed to associate only differences of greater than a predetermined amount with the presence of deposits such as plaque, for example within the limits mentioned above.

A further aspect of this invention is based upon the fact that dental plaque on a tooth surface has its own inherent auto fluorescence, for example as discussed in the state of the art referred to above, e.g. U.S. Pat. No. 5,382,163, DE 29704185, DE 29705934, EP 0774235, and also WO 97/01298 which disclose wavelengths at which such auto fluorescence is emitted, for example above ca. 600 nm.

Auto fluorescence emission when biological deposits on tooth surfaces, believed to be dental plaque, are illuminated with radiation at wavelengths below ca. 50 nm, preferably <450 nm has been discovered, with emission maxima between ca. 530 nm and ca. 630 nm, in particular having two emission maxima, one at ca. 540–550 nm and another at ca. 610–620 nm. The discovery of these two maxima is believed to be novel.

When only a small amount of biological deposit is present on the teeth then the auto fluorescence associated with tooth surfaces free or substantially free from biological deposit may be so intense that the auto fluorescence emission from the deposit itself or its constituents such as dental plaque is not observed, i.e. it is swamped by the auto fluorescence associated with tooth surface material itself. However as the amount of biological deposits such as plaque on the tooth increases and/or the age of the deposit increases the auto fluorescence emitted by the deposit itself or its constituents such as dental plaque generally increases until this auto fluorescence is of such an intensity that it can be detected in spite of the auto fluorescence associated with tooth surfaces free or substantially free from biological deposits. When the deposit is very thick or aged the auto fluorescence emission from the deposit itself or its constituents dominates and can be easily measured in spite of the auto fluorescence associated with tooth surface material itself.

Consequently a continuum exists in that when only small quantities of deposit or only a thin layer of biological deposit are present then the apparatus and method of the first aspect of this invention as described above may be used to detect the biological deposit, and when more biological deposit is present measurement of the auto fluorescence emissions from the biological deposit or its constituents such as plaque itself may be used.

Therefore in a preferred embodiment of this invention, the apparatus of the invention additionally comprises;

- detection means to detect auto fluorescence emission from the test tooth surface at a wavelength associated with auto fluorescence emission from biological deposits on a tooth surface, and
- means to relate this auto fluorescence emission to the presence of biological deposit on the test tooth surface, and
- indicator means to indicate the presence of biological deposit to a user of the apparatus.

Preferably the detection means is capable of detecting auto fluorescence emission from the test tooth surface at a wavelength associated with auto fluorescence emission from dental plaque on the tooth surface.

These detection means may detect auto fluorescence emission from the biological deposits being of the wavelengths associated with autofluorescence from dental plaque disclosed in the state of the art discussed above. Preferably the means detects either or both of the emission maxima between ca. 530 nm and ca. 630 nm referred to above.

The use of this auto fluorescence emission, referred to above, from biological deposits such as dental plaque deposits on tooth surfaces is itself believed to be novel. Therefore in a further aspect of this invention, an apparatus for the detection of biological deposits on a test surface of a tooth, in particular dental plaque, is provided comprising;

- detection means for the detection of auto fluorescence emission from biological deposits on a test tooth surface between ca. 530 nm and ca. 630 nm;
- means to relate this auto fluorescence emission from the biological deposits to the presence of biological deposits on the test tooth surface and;
- indicator means to indicate the presence of biological deposits to a user of the apparatus.

Preferably the detection of auto fluorescence is carried out at one or both of the two emission maxima mentioned above, i.e. the one at ca. 540–550 nm and another at ca. 610–620 nm.

Suitably the auto fluorescence emission from biological deposits is produced by means to direct exciting radiation onto a test tooth surface. This exciting radiation may be exciting radiation at the wavelength used in the apparatus of the first aspect of this invention.

Suitably the illumination means for the above aspects and preferred embodiments of this invention may comprise a light emitter such as a light emitting diode (LED) capable of emitting radiation in the blue region of the visible spectrum, preferably including radiation between 430 and 500 nm. Such LED's, emitting radiation at 480±50 nm are commercially available. The LED should preferably be of low power to minimize consumption, and LED's operating at a power of 5–20 mA are suitable.

The exciting radiation from such an LED may be directed to the tooth surface by a light guide, for example one or more, e.g. a bundle, of optical fibres. Conventional commercially available optical fibres may be used, and preferably for insertion into the user's mouth plastic material rather than glass fibres are used, to minimize any risk of breakage or scratching of the user's gums or other parts of the user's mouth tissues. Suitable materials for the optical fibres should not emit any fluorescence when illuminated with the exciting radiation. Optical fibres of ca. 0.25–2.0 nm (i.e. 250 micron–2.0 nm) have been found suitable for this purpose, and a bundle of these up to ca. 4 mm is found suitable, depending on the area of tooth surface that is to be tested for biological deposits such as dental plaque. It may be appropriate to incorporate optical filters into the optical path between the light emitter and the test tooth surface to ensure that excitation radiation of wavelengths that causes fluorescence emission is preferentially directed to the test tooth surface. It may also be appropriate to incorporate focusing optics, e.g. one or more lenses, into the optical path between the light emitter and the test tooth surface to ensure that exciting radiation is focused and concentrated onto the test tooth surface.

If the illumination means emits radiation with a wavelength below ca 420 nm then it is preferred, for safety reasons, to include a cut-off filter to prevent such radiation reaching the tissues of the user. Suitable filters of this type are known. A suitable type of filter is a dichroic filter, e.g. dichroic mirrors which reflect at the wavelength of the exciting radiation and transmit at the wavelength of the emitted fluorescence radiation, which are preferred as a cheap and convenient way of cutting out such low wavelength radiation.

The detector means may comprise a conventional detector e.g. a semiconductor photodiode. It may be appropriate to incorporate optical filters into the optical path between the detector and the test tooth surface to ensure that fluorescence emission is preferentially guided to the detector. It may also be appropriate to incorporate focusing optics, e.g. one or more lenses, into the optical path between the detector and the test tooth surface to ensure that fluorescent emission is focused and concentrated onto the detector. The detector means may also comprise a light guide, for example one or more optical fibres, e.g. a bundle as described above, to guide fluorescence emission from the tooth surface to a detector for the fluorescence emission radiation.

Although separate light guides for the exciting radiation and fluorescence emission radiation may be used, alternatively a single light guide may be used for both over part of the length of the light guides and a beam splitter/combiner of known type may be used to separate the excitation and emission radiation and guide them as appropriate. For example the same optical fibres may be used for guiding both the exciting and emitted fluorescence radiation, and the exciting and emitted fluorescence radiation may be filtered using dichroic filters.

It is preferred to modulate and/or phase lock the excitation radiation and the detection of the fluorescent emission e.g. at 20–500 Hz, e.g. at 100–300 Hz, suitably at around 200 Hz, in synchronisation so that the fluorescence emission can easily be distinguished from unmodulated background radiation, e.g. from light sources outside the user's mouth. Preferably modulation at around electric mains frequency (generally 50–60 Hz) and multiples thereof should be avoided to avoid interference from electric lights in the environment of the user.

In a preferred embodiment of this invention optical fibres comprising the light guide of the illumination means and the detection means may be bundled together within a suitable conduit, and may terminate at a common optical probe, for example a transparent cover or a focusing transmitting/collecting probe. Such a probe may incorporate one or more lenses which may focus exciting radiation from the illumination means onto the test tooth surface and may focus fluorescence emission from the test tooth surface into the light guide. The optical fibres may be bundled together randomly. Alternatively they may be bundled such that the fibre(s) comprising the light guide of the illumination means or alternatively the fibre(s) comprising the light guide of the detection means may comprise a central core, surrounded by a ring or polygon of fibres comprising respectively the light guide of the detection means, or the light guide of the illumination means. If separate optical fibres are used as light guides for the excitation and emission radiation then preferably a greater number of fibres is used for the light guide of the emission radiation than for the excitation radiation because of the lower intensity of the fluorescence emission radiation.

The means to indicate the presence of biological deposits such as dental plaque to a user of the apparatus may comprise an electronic means which gives a visual, e.g. a light, signal or an audible, e.g. a sound, signal to a user to indicate the presence of such biological deposits. For example the means may give such a signal only when a significant amount of biological deposit is present, and cease to give this signal when the deposit has been removed, or alternately the means may give no signal when biological deposit is present but may give such a signal when the deposit is absent. Alternative indicator modes will be apparent to those skilled in the art. The construction of such a means will be readily apparent to those skilled in the art of electronics.

In a preferred embodiment of this invention the apparatus comprises a toothbrush, for example having means to direct exciting radiation at the test tooth surface and the means to detect fluorescence emission from the test tooth surface incorporated into the toothbrush head, e.g. having one or more optical fibres as described above incorporated and terminating at an optical probe in the toothbrush head, so that the optical probe can be conveniently close to the test tooth surfaces of a user, e.g. within 1 cm or less, being approximately the usual length of toothbrush bristles. Such a toothbrush may also incorporate conventional cleansing bristles in its head, and in one embodiment the cleansing bristles may themselves comprise or incorporate one or more such optical fibres to thereby comprise a probe. The toothbrush may be a toothbrush used by hand action, or more conveniently may be an electric toothbrush, i.e. in which the brush head incorporating the bristles is driven by an electric motor.

The head incorporating the probe may be a permanent part of the toothbrush or alternately and preferably may be replaceable. Conveniently the illumination means, detection means and the various electronic signal/data processing means etc., and a suitable electrical power supply, e.g. a battery or electrical mains connection, may be provided in the handle of the toothbrush. If such a toothbrush has an electrically driven cleaning brush then in such a construction all of the electrical components, e.g. the drive motor etc., can be incorporated into the toothbrush handle.

If the device of the invention is incorporated into a toothbrush then it may be constructed so as to indicate the initial presence of biological deposits on the surface of the user's teeth and indicate the quantitative reduction or absence of biological deposits after the teeth have been brushed for a suitable period. Such a toothbrush may be constructed to indicate to the user that biological deposits are present somewhere in an area of the user's teeth, and thus that continued brushing of the teeth is necessary to remove the deposits.

Accordingly the invention also provides a toothbrush which incorporates a device as described above. Preferably such a toothbrush is constructed provided with means to indicate to the user that deposits initially present on the teeth have been removed by the process of brushing the teeth, and/or means to indicate to the user that deposits are still present even after a period of toothbrushing, and that brushing needs to be continued.

Alternately the apparatus may comprise a dental tool, for example a dental tool suitable for use by a dentist carrying Out an in vivo examination of his/her patient's teeth.

In use the test tooth surfaces may be initially cleaned, e.g. by a preliminary rinse, to remove dirt and other loosely held deposits and contaminants which might obscure the test tooth surface and then apply the apparatus to the test tooth surface. When the apparatus indicates to the user that biological deposit such as plaque is present on the test tooth surface the surface may be cleaned, for example using toothbrush bristles and optionally a dentifrice composition such as a toothpaste, and the apparatus re-applied to the test tooth surface to determine whether the deposit is still present. If deposit is still present the procedure is repeated until the apparatus indicates that the deposit has been removed. Alternatively and particularly if the device comprises a toothbrush, it may simply be applied to the teeth in a toothbrushing process and toothbrushing is continued until the device indicates that deposits have been removed to a satisfactory extent. If a dentifrice is used in the toothbrushing process, preferably it is a dentifrice which contains no constituents which exhibit fluorescence at the wavelengths of fluorescence emission which are detected by the detection means.

The invention will now be described by way of example only with reference to the following figures.

Figure 1:
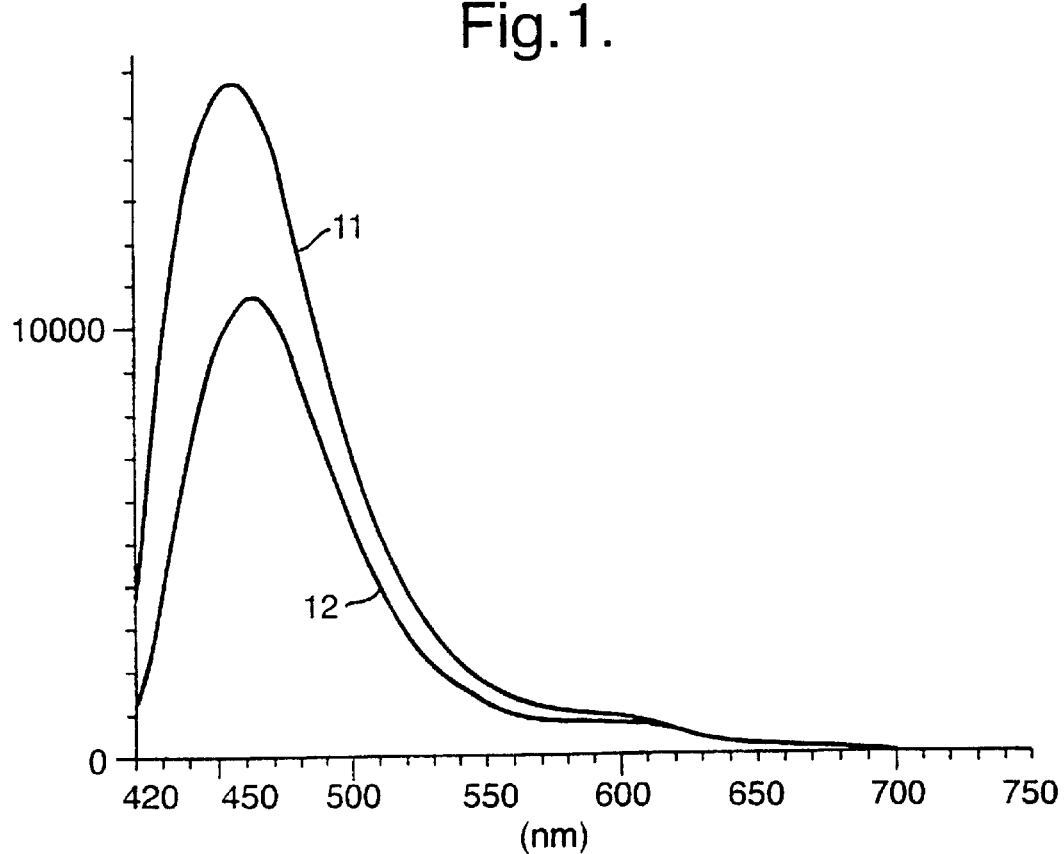
FIG. 1 Shows an intensity/wavelength graph of auto fluorescence emission from a biological deposit-free test tooth surface and auto fluorescence emission from a test tooth surface on which is a deposit of dental plaque over an emission wavelength range 420–750 nm.

Referring to FIG. 1, the wavelength (nm) of auto fluorescence emission is shown on the horizontal axis and the intensity (arbitrary units) is shown on the vertical axis. A clean test tooth surface, being free of biological deposits having been cleaned by known methods to remove biological deposits, was illuminated with exciting radiation of wavelength <420 nm. and the intensity of the resulting auto fluorescence from the deposit-free surface was measured, using a conventional epifluorescence detection microscope. The intensity/wavelength graph of this emission is shown as line 11 of FIG. 1. A strong emission maximum is observed at ca. 450 nm. The tooth surface was then covered with a layer of fresh dental plaque, and the intensity of the resulting auto fluorescence from the tooth surface upon illumination with exciting radiation of wavelength <420 run was again measured as above. The intensity/wavelength graph of this emission is shown as line 12 of FIG. 1. It is seen that the magnitude of the emission intensity peak at ca. 410 nm is substantially attenuated.

Figure 2:
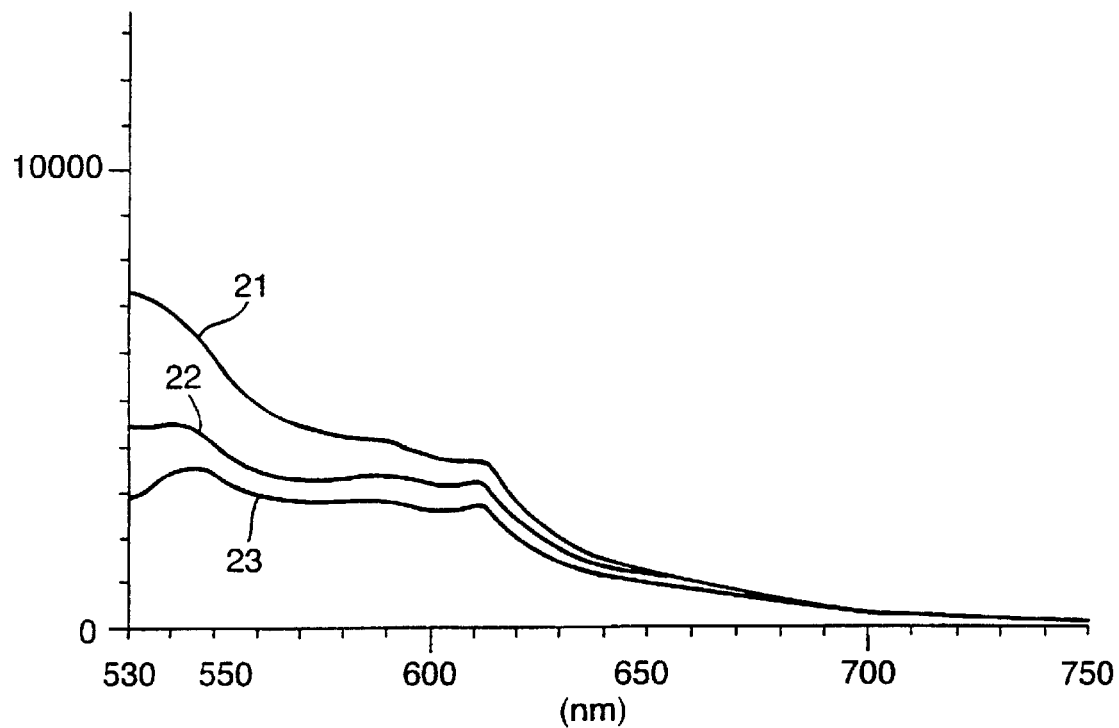
FIG. 2 Shows an intensity/wavelength graph of auto fluorescence emission from a biological deposit-free test tooth surface and auto fluorescence emission from a test tooth surface on which is a biological deposit at wavelengths above 530 nm in more detail.
Figure 2:
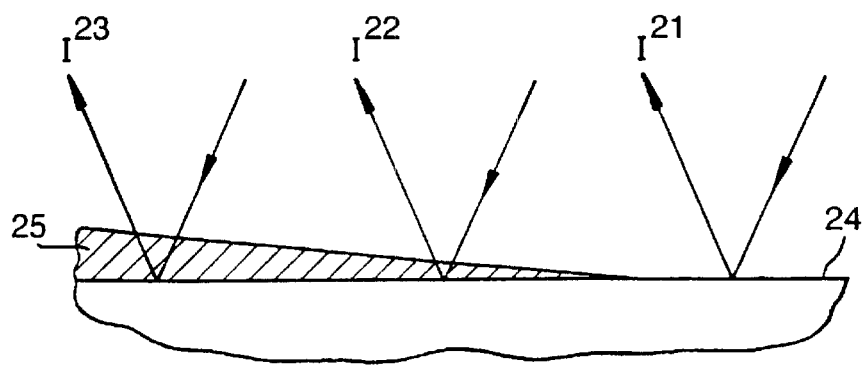

Referring to FIG. 2, the wavelength (nm) of auto fluorescence emission is shown on the horizontal axis and the intensity (arbitrary units) is shown on the vertical axis. In FIG. 2 the region of the graph of FIG. 1 showing intensity of auto fluorescence at wavelengths above 530 nm is shown at greater amplification. Line 21 of FIG. 2 shows the intensity of auto fluorescence with a substantially biological deposit-free tooth surface, and lines 22 and 23 of FIG. 2 show the intensity of auto fluorescence with progressively increasing amounts of biological deposit present. It is seen that at these higher wavelengths, which may be produced using exciting radiation below 530 nm, the attenuation of intensity of the fluorescence emission is sufficient to be easily detected.

FIG. 2 also shows schematically a section through a tooth having a surface of clean enamel 24, upon which there is a progressively thickening biological deposit such as dental plaque. Intensities of fluorescence emission from areas of the tooth are shown as $I^{21}$, $I^{22}$ and $I^{23}$ respectively corresponding to a clean area and thicker areas of plaque.

Figure 3:
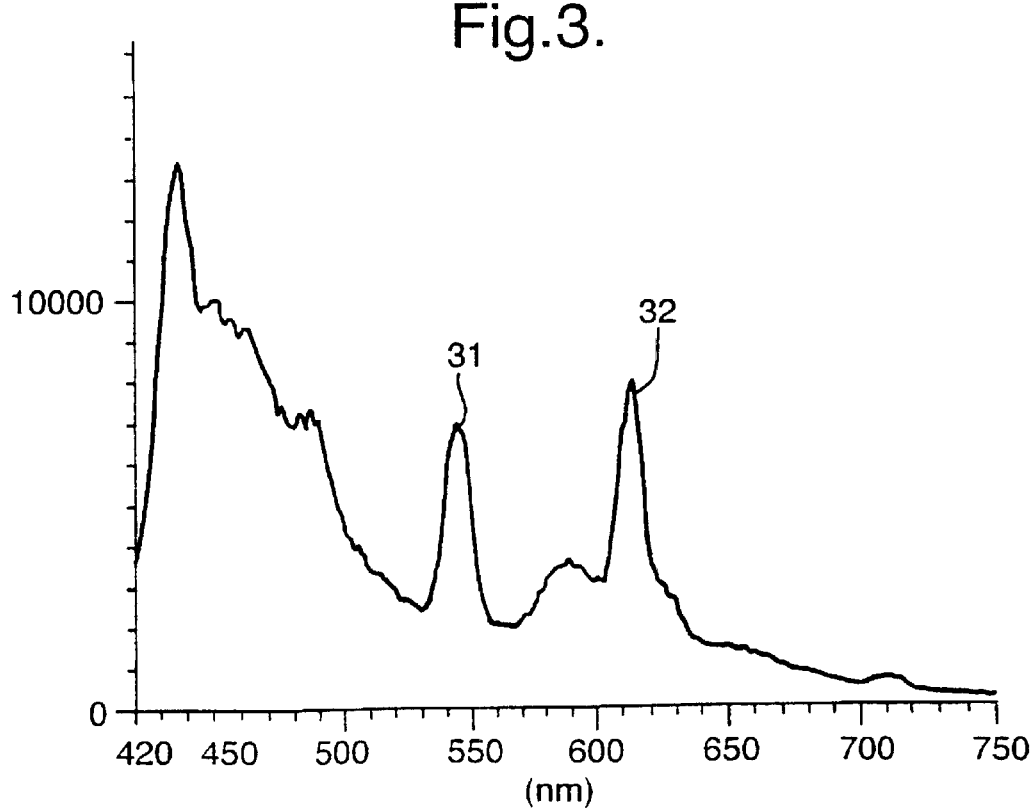
FIG. 3 Shows an intensity/wavelength graph of auto fluorescence emission from dental plaque.

Referring to FIG. 3, the wavelength (nm) of auto fluorescence emission is shown on the horizontal axis and the intensity (arbitrary units) is shown on the vertical axis. A test tooth surface on which there was a thick deposit of a biological deposit believed to be fresh dental plaque was illuminated with exciting radiation of wavelength <420 nm. and the intensity of the resulting auto fluorescence from the deposit- covered surface was measured, using a conventional epifluorescence detection microscope. Strong emission maxima are observed between ca. 530 nm and ca. 630 nm, in particular two emission maxima, one at ca. 540–550 nm, peak 31 of FIG. 3, and another at ca. 610–620 nm, peak 32 of FIG. 3.

Figure 4:
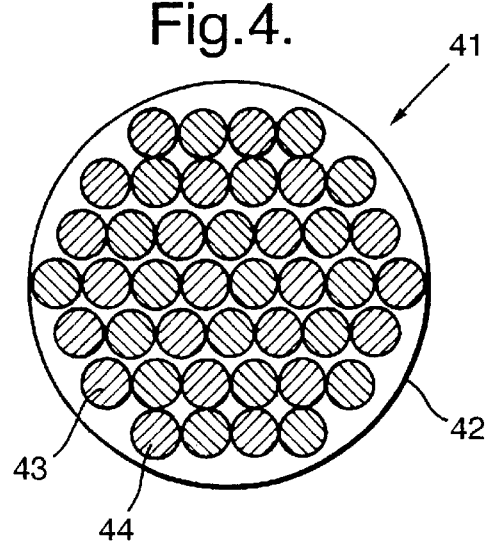
FIG. 4 Shows a cross section through a light guide comprising optical fibres for the illumination and detection means.

Referring to FIG. 4, part of a light guide, 41 overall is shown in cross section. The light guide 41 comprises a conduit 42, within which is a bundle of optical fibres 43, 44, comprising light guides 43 for the exciting radiation and light guides 44 for the emission radiation. These fibres 43, 44 are arranged in a random bundle, there being more fibres 44 for the emission radiation than fibres 43 for the exciting radiation because of the lower intensity of the emission radiation.

Figure 5:
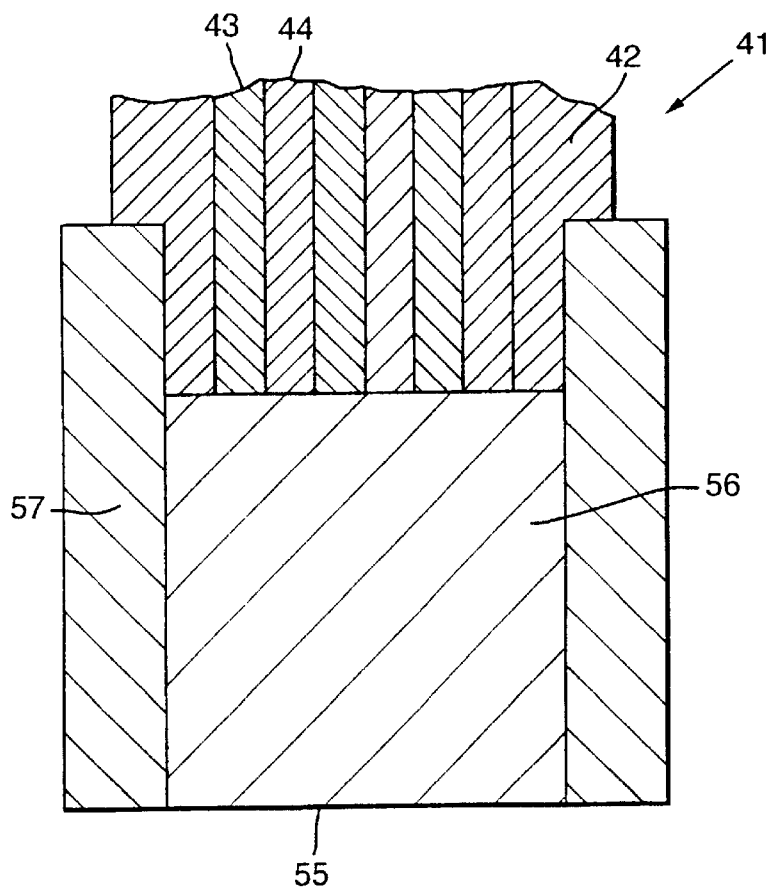
FIG. 5 Shows a longitudinal section through a probe of the apparatus of this invention.

Referring to FIG. 5 a probe incorporating the light guide 41 is shown in longitudinal section. Parts corresponding to FIG. 4 are correspondingly numbered. The fibres 43, 44 terminate at a common probe surface 55, behind a transparent probe cover 56, held within an end cap 57 forming a probe. In use the front of the surface 55 may be positioned in close proximity to the test tooth surface.

Figure 6:
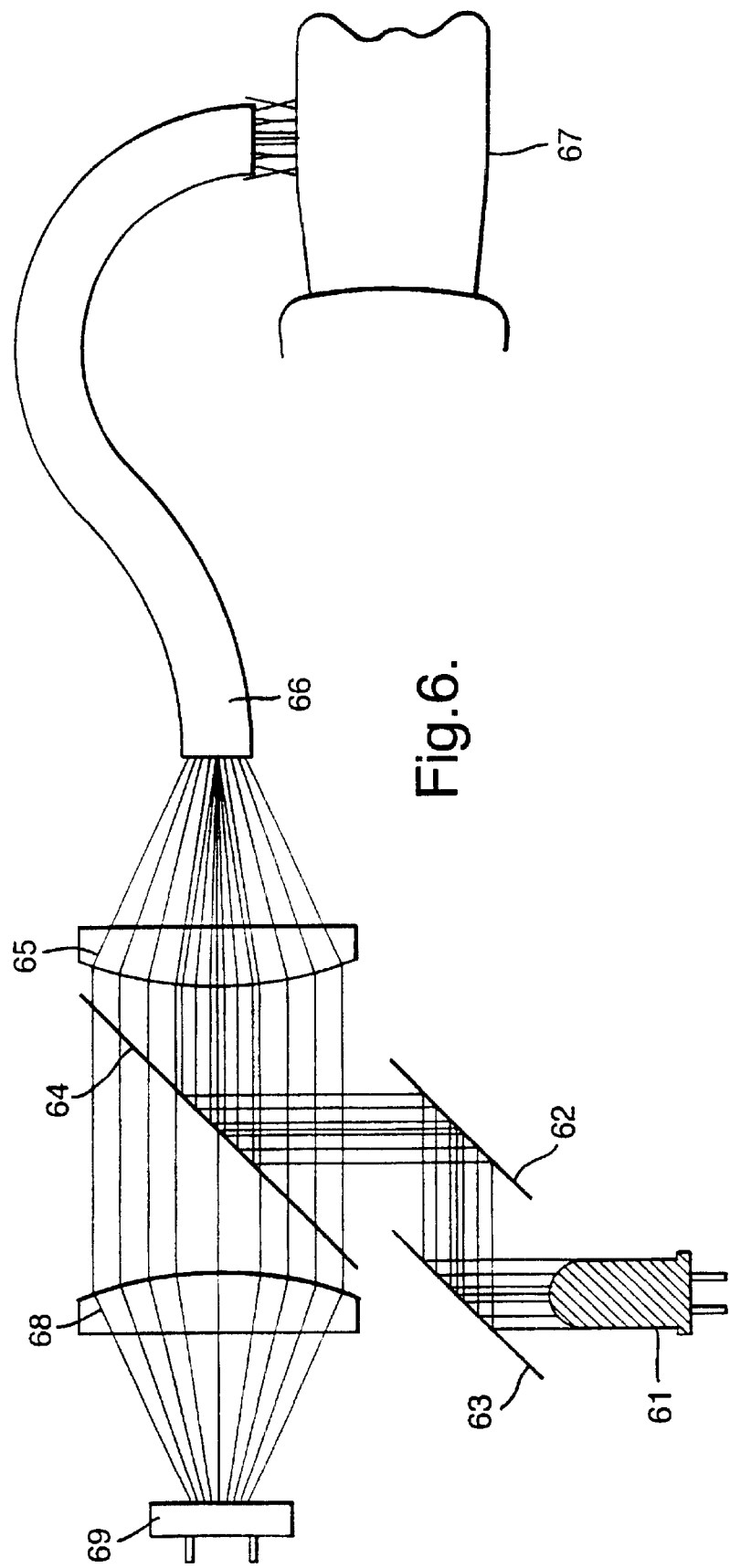
FIG. 6 Shows a schematic layout of an optical system for the apparatus of this invention.

Referring to FIG. 6, this shows a schematic layout of an optical system for the apparatus of this invention. Exciting light of wavelength 480 nm+50 nm (blue) is produced by LED 61. A series of three dichroic mirrors 62, 63, 64 direct light of wavelength above 480 nm towards a focusing lens 65 which focuses this light toward the light guide 66. These dichroic mirrors prevent any significant amount of light of wavelength below 480 nm from being directed onto the tooth surface, to minimize any risk of injury to the user from such light. Light guide 66 is a bundle of optical fibres, along which the light is guided onto the surface of a tooth 67, and along which fluorescence emission radiation is returned. The lens 65 focuses the fluorescence emission radiation, and dichroic mirror 64 transmits only radiation above 530 nm to the lens 68 which focuses this radiation onto the detector 69.

Figure 7:
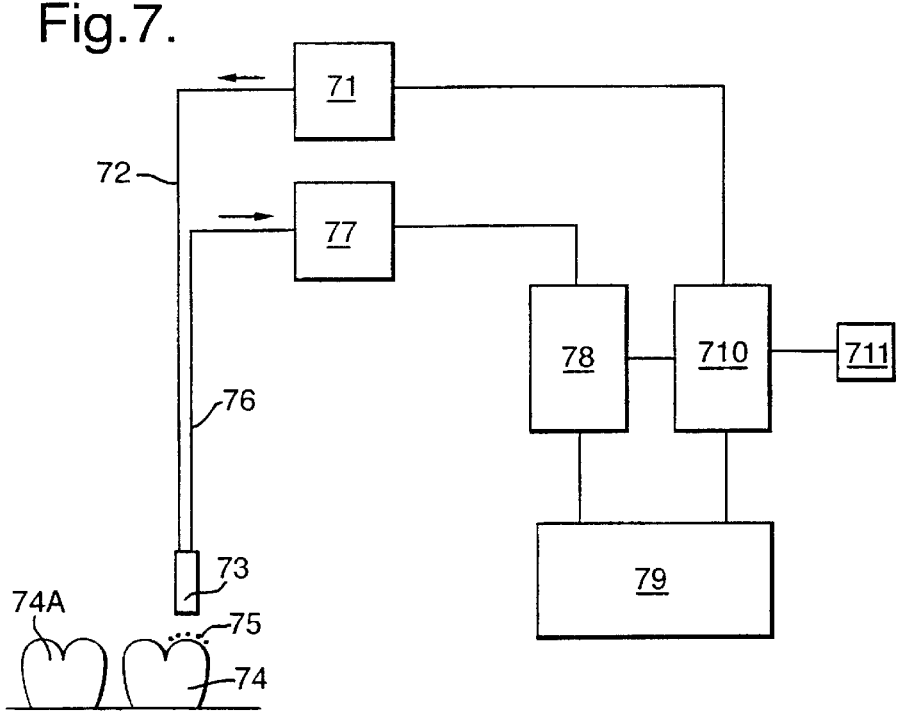
FIG. 7 Shows a schematic layout of the apparatus of this invention in use.

Referring to FIG. 7, a schematic layout of the apparatus of this invention is shown. The apparatus comprises an illumination means, which itself comprises a light emitter 71 in the form of an LED and a focusing system to guide exciting radiation, i.e. light emitted by the LED along a light guide 72 comprising a bundle of optical fibres to direct exciting radiation from probe 73, being a probe as shown in FIGS. 4 and 5, onto a test tooth surface 74 upon which is a deposit such as dental plaque 75. Fluorescence emission from the tooth surface 74 and/or the deposit 75 is collected by the probe 73 and is guided by the light guide 76 comprising a bundle of optical fibres to a detection means 77. This detects fluorescence emission from the test tooth surface 74. This emission may be at a wavelength associated with that of auto fluorescence emission from a substantially deposit free tooth surface and/or auto fluorescence emission from the deposit 75.

An electronic signal from the detection means 77 is passed to the signal/data processing means 78. This means 78 may comprise means to make a comparison of the intensity of the auto fluorescence emission from the test tooth surface with an intensity of auto fluorescence emission associated with auto fluorescence emission from a substantially biological-deposit free tooth surface and means to associate the comparison thus obtained with the presence of deposit on the test tooth surface, and/or means to relate auto fluorescence emission from the deposit to the presence of deposit on the test tooth surface. The signal/data processing means 78 may suitably comprise a microprocessor device, and may be pre-loaded with standard reference intensity data e.g. relating to the intensity of fluorescence emission from a substantially biological deposit-free tooth surface, and/or reference intensity date relating to auto fluorescence emission from dental plaque.

The electronic output from the signal/data processing means 78 is sent to indicator means 79 to indicate the presence of biological deposits e.g. dental plaque to a user of the apparatus by means of an appropriate signal, for example to indicate that deposit is absent or alternatively that deposit is present, or that deposit which was present has been removed.

The illumination means 71, signal/data processing means 78 and the indicator means 79 are all powered by an electrical power supply 710. The power supply 710 may be a modulated power supply, for example under the control of the signal/data processing means 78. The entire apparatus is under the control of the user via control 711, which may comprise a simple on/off switch and/or a mode selector switch, for example to determine the nature of the signal to be given by the indicator means 79, and/or the mode of operation of the apparatus, i.e. whether it is to detect a wavelength of fluorescence emission associated with a substantially biological deposit-free tooth surface, or fluorescence emission from biological deposits, or both.

In use the probe 73 is placed closely adjacent to a test tooth surface 74. Exciting radiation emitted by the emitter 71 is directed via light guide 72 to the surface 74, and fluorescence emission radiation, which may be fluorescence emission at a wavelength corresponding to that from a substantially biological deposit-free tooth surface, or auto fluorescence emission from biological deposit, is collected by the probe 73 and directed via light guide 76 to detection means 77. The operation of emitter 71 and detector 77 are modulated in synchronisation. The electronic signal from the detector 77 is inputed to signal/data processing means 78, and the consequent output signal in response from the data/signal processing means 78 is inputed to indicator means 79, to provide an appropriate signal to the user.

In one mode of use the probe 73 is placed closely adjacent to a reference tooth surface 74A which is known to be free of biological deposit, such as a surface of the user's front teeth, and the fluorescence emission, which may be fluorescence emission at a wavelength corresponding to that from a substantially biological deposit free tooth surface, or auto fluorescence emission from a biological deposit such as plaque is collected by the probe 73 and directed via light guide 76 to detection means 77, in a modulated manner as above. The electronic signal from the detector 77 is inputed to signal/data processing means 78, and this signal may be used to generate intensity reference data for the subsequent use of the apparatus to detect dental biological deposits such as plaque in the test tooth surface 75, i.e. being compared in the signal/data processing means 78 with fluorescence emission test data from the test tooth surface 74. In such a mode the indicator means 79 may indicate to the user that such reference data has been generated.

Figure 8:
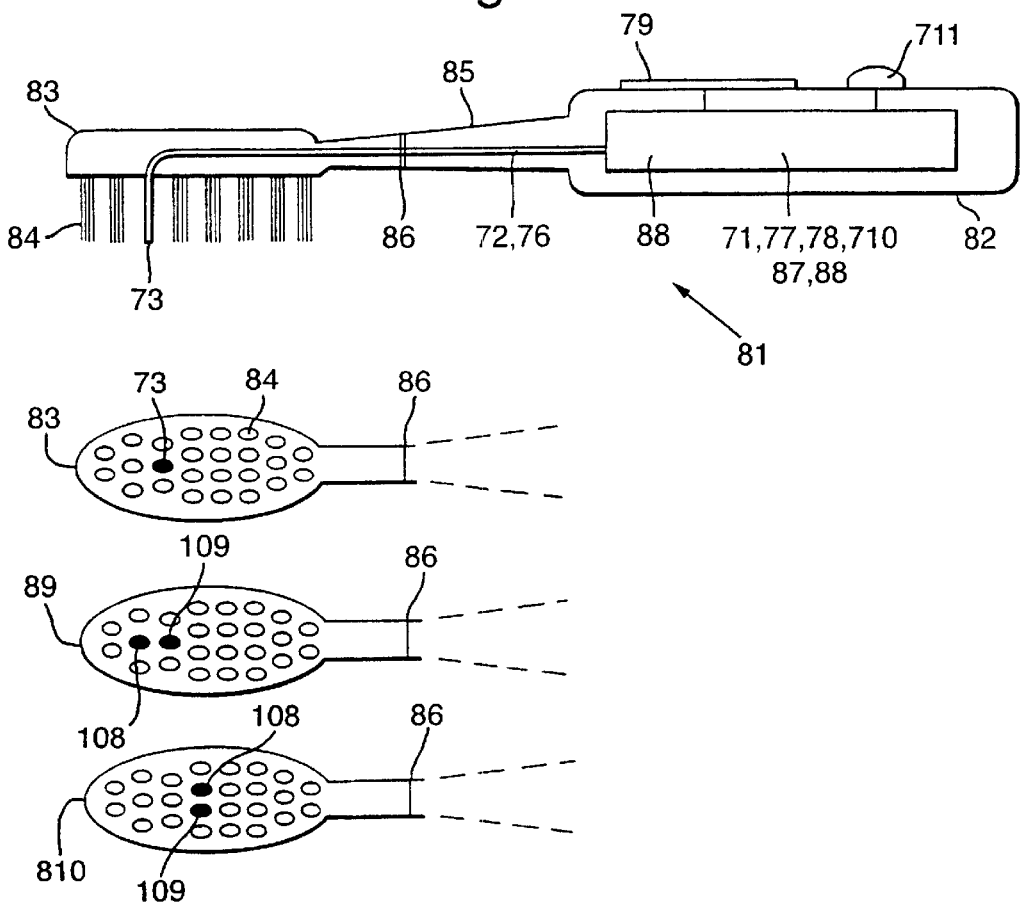
FIG. 8 Shows schematically a toothbrush of this invention.

Referring to FIG. 8 a toothbrush 81 overall is shown schematically. The toothbrush 81 comprises a handle 82, a head 83 which carries tufts of cleaning bristles 84, and a connecting neck region 85 between them. The head 83 is replaceable by being removable from the neck 85 at the connection 86. Projecting from the head 83, parallel to the bristles 84 is a probe 73, having the general construction as shown in FIG. 5, i.e. being a soft, flexible bundle of optical fibres, approximately the same in length, diameter and texture to the tufts of bristles 84. One probe 73 is shown but the head 83 may include two or more. The probe 73 is connected by light guides 72, 76 to the handle 82, which includes an LED light emitter 71, detection means 77, signal/data processing means 78 and power supply 710, and with an indicator means 79 and control 711 on its outer surface. The connection 86 is constructed such that a good optical connection is made between the probe 73 and the handle 82.

In use the toothbrush is switched on by means of the control 711 and used for brushing the teeth. The probe 73 detects the presence of biological deposits using processes as described herein, and indicates the presence of deposits to the user by means of the indicator means 79. The indicator means 79 may also indicate to the user such things as the fact that the device is switched on, low battery power, a faulty connection at 86 or the need to replace the head 83 because for example the probe 73 on bristles 84 have worn out. If the toothbrush 81 indicates to the user that dental deposits are present the user may continue to brush the teeth until the deposits have been removed. The handle 82 may also include an optional motor 87 and drive means 88 which drives an electric toothbrush head 83.

FIG. 8 also shows two toothbrush heads 89, 810 having two probes 73. In head 89 these two probes 73 are spaced apart along the longitudinal head-handle axis of the toothbrush 81, and in head 810 these two probes 73 are spaced across the width axis (i.e. the direction perpendicular to the longitudinal head-handle axis) of the toothbrush 81. The heads 89, 810 may be replaceable heads suitable for use with the handle 82 shown in FIG. 8. The use of multiple pairs of probes 73 as shown in FIG. 8 can enable more areas of the teeth to be tested simultaneously, or via the internal electronics and software of the device can provide a more accurate detection of biological deposits. Alternatively the two probes 73 present in the heads 89, 810 may be used as the two probes referred to later with reference to FIG. 10.

Referring to FIG. 9 one method of use of the device of the invention is shown. FIG. 9A shows a schematic view of a set of teeth 91, 92, 93, 94 extending from a user's gumline 95, and show distance across the set of teeth 91, 92, 93, 94. Areas on which there are biological deposits are shown 91A, 92A, 93A, and there are also gaps 96, 97, 98 between the teeth, and tooth 94 has an amalgam filling 99.

A probe of the type 41, 73 incorporated in a toothbrush head as shown in FIG. 8 is moved in the irregular path A—A across the teeth 91–94 for example during toothbrushing. In the course of this path the probe 41, 73 encounters the areas 91A, 92A and 93A where there are biological deposit, the gaps 96, 97, 98 and the filling 99 as well as clean areas where there are no biological deposits, i.e. the clean areas shown on the teeth 91–94.

Figure 9A:
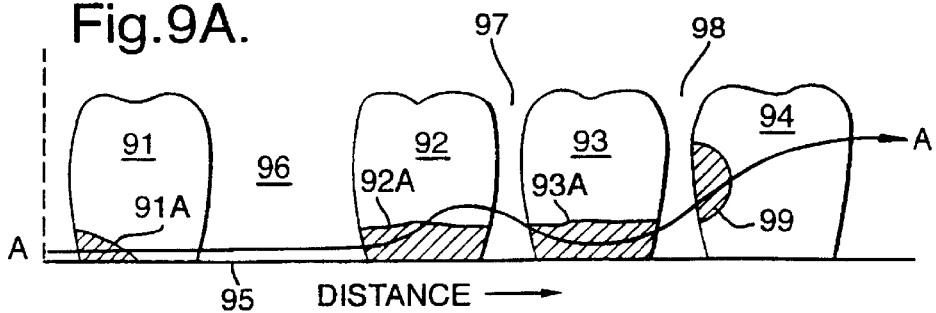
FIG. 9 Shows a mode of use of the device of the invention.
Figure 9B:
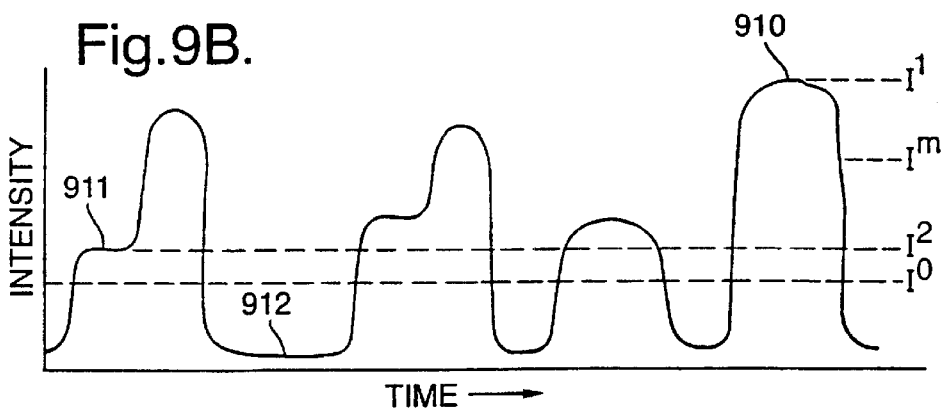

FIG. 9B shows a graph of fluorescence emission I from the surfaces of teeth 91–94 as detected by the probe 41, 73 as it moves across the teeth 91–94 on the path A—A, with time, that is in a "dynamic" measurement. The graph of fluorescence intensity against time shows high peaks and plateaus 910 corresponding to the clean areas of the teeth 91–94, lower peaks and plateaus 911 corresponding to the regions of the teeth 91–94 where there are biological deposits, and minima 912 corresponding to the gaps 96, 97, 98 and the filling 99.

The highest of the high peaks 910 has a fluorescence intensity $I^1$, and the lowest of the low peaks 912 has a fluorescence intensity $I^2$. A lower limit $I^0$ is set, above the intensity of the minima 912 but below the level $I^2$, and the device is set to ignore any fluorescence emission intensity during use less than $I^0$. The presence of biological deposits is indicated by $I^1$–$I^2$ being greater than zero. The device may be set to associate magnitudes of $I^1$–$I^2$ greater than a certain level with the presence of biological deposits, and to indicate to the user on the basis of this that deposits 91A, 92A and 93A are present. The device may also be constructed to calculate the mean fluorescence emission intensity $1'''$.

Figure 9C:
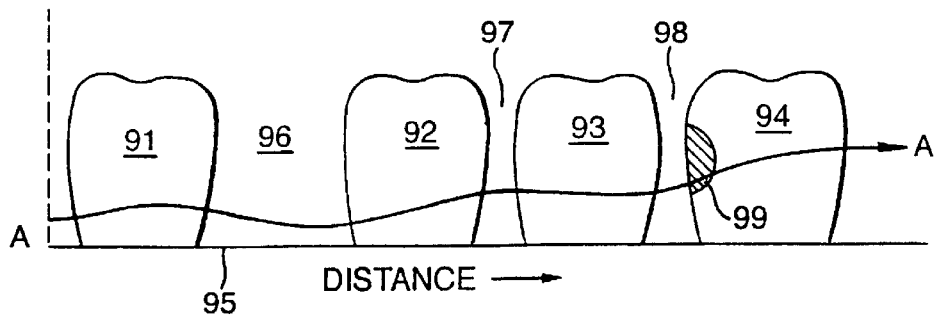
Figure 9D:
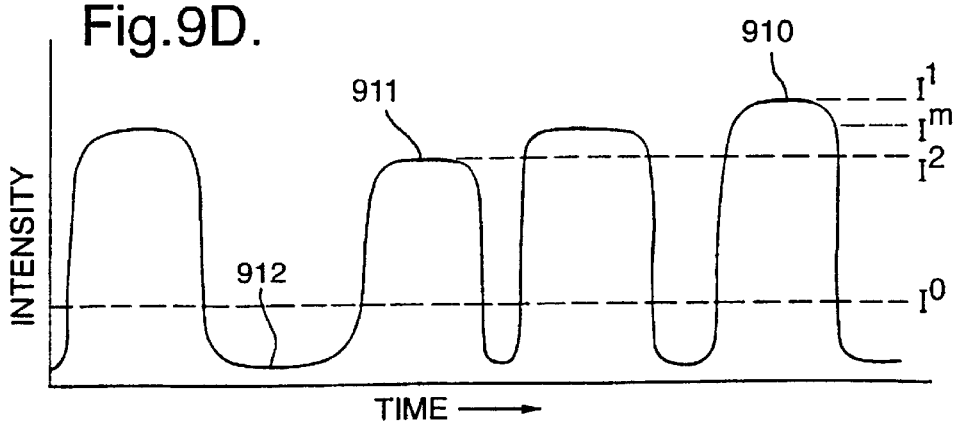

FIG. 9C shows a set of teeth 91–94 the surfaces of which are clean of biological deposits. A probe of the type 41, 73 is moved across the surface of the teeth 91–94 and a corresponding fluorescence intensity/time graph is produced as shown in FIG. 9D. As is seen from FIG. 9D, the difference $I^1-I^2$, though still greater than zero is significantly less than the $(I^1-I^2)$ value of FIG. 9B. This reduced $(I^1-I^2)$ value of FIG. 9D may be less than a certain level set in the software and/or electronics of the device and may indicate to the user that the surfaces of the teeth 91–94 are adequately clean of biological deposits. FIG. 9D also shows that the mean fluorescence emission $I'''$ also increases as deposits 91A, 92A and 93A are removed.

If the device used in FIG. 9 is a toothbrush, e.g. as shown in FIG. 8 then it may be set to indicate to the user that tooth rushing needs to be continued whilst $I^1-I^2$ remains above the certain set level.

Figure 10:
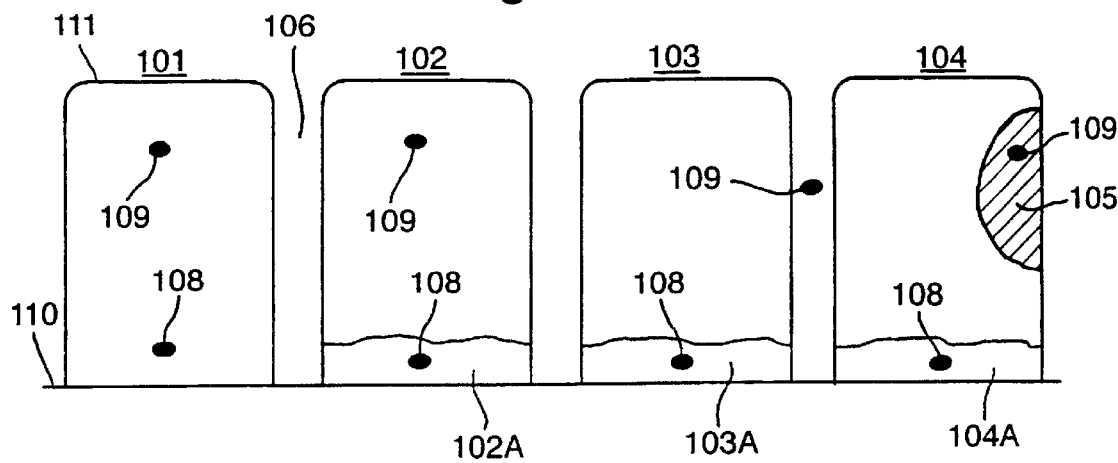
FIG. 10 Shows another mode of use of the device of the invention.

Referring to FIG. 10 four representative teeth 101, 102, 103, 104 are shown, three of which, 102, 103, 104 have areas of biological deposit 102A, 103A, 104A on them, tooth 101 being entirely clean, and tooth 104 having an amalgam filling 105. There are gaps 107 between the teeth. Two probes 108, 109 of the type 41, 73 are applied to the surface of the teeth 101, 102, 103, 104. The spacing "d" of the probes 108, 109 is approximately 80% of the height of a tooth from the gumline 110 to the crown 111. The intensity of fluorescence emission detected by each of the probes 108, 109 and their relative intensities are measured and compared by the electronics and software of the device.

On tooth 101 the intensities of the fluorescence emission detected by the two probes 108, 109 is substantially identical or differs only by less than a certain level set by the limits set by the software and electronics of the device. This small difference is used to indicate to the user that the tooth 101 is clean of dental deposits.

On tooth 102 the probe 108 detects fluorescent emission from a clean part of the tooth surface, and the probe 109 detects fluorescent emission from an area 102A of the tooth surface where there are biological deposits. The intensities of the fluorescent emission detected by the two probes 108, 109 differ, that detected by probe 109 being less than that detected by probe 108. This difference is however within limits set by the internal electronics and software of the device, and is used to indicate to the user the presence of the biological deposits on the tooth 102.

On tooth 103 the probe 108 detects fluorescent emission from a region 103A of the tooth 103 where there is biological deposit, and probe 109 is located at a gap between the teeth. On tooth 104 the probe 108 detects fluorescent emission from a clean region of tooth 104, and probe 109 is adjacent an amalgam filling 110, from which there is no fluorescent emission. With both teeth 103 and 104 the difference between the fluorescent emission detected by the probes 108 and 109 is greater than the limits preset in the electronics and software of the device and is ignored by the device, so that no false reading is given.

The toothbrush heads 89 ad 810 shown in FIG. 8 include two probes suitable for use in the process described with respect to FIG. 10.

Experimental data illustrating the invention is presented below.

1. Device Construction

In the experiments the illumination source was an LED emitting radiation of 470 nm±40 nm, and the excitation filter allowed radiation through of wavelength 355–490 nm onto the teeth surfaces. The barrier filter allowed through radiation of greater than 520 nm and the dichroic mirror filtered light above 510 nm to be detected as fluorescence emission.

2. Basic Data

A sample of 16 volunteers were taken and received a thorough professional tooth cleaning. The fluorescence emission data were recorded of the buccal aspects (exactly at the central point of the equators) of all teeth in the $1^{st}$ and $4^{th}$ quadrant (teeth 11 to 17 maximillary, teeth 41–47 mandibular). In most cases the sound enamel was assessed but in a few cases fillings were present and in these cases the fluorescence signals from the fillings was recorded.

It was found that the fluorescence intensity of clean teeth rose with increasing "tooth number", i.e. location or tooth type respectively, the exception being the last molars (17 and 47). This fluorescence from clean tooth surfaces existed, but it was also found that the inter-individual differences were less pronounced. It was also found that the intensity of fluorescence emission from dental restorative materials was very low (generally $\leq 1.0$), as indicated below:

| Material | No. measurements | Range |
| --- | --- | --- |
| Amalgam | 2 | 0.05–0.06 |
| Gold | 4 | 0.12–0.15 |
| Ceramic | 13 | 0.01–0.14 |
| Composite | 4 | 0.08–0.12 (one at 1.04) |
| Enamel | 195 | 1.00–>3.4 |

This indicated that little problem would occur from fluorescence emission from such restorative materials.

3. Plaque Detection 4 volunteers refrained from all mechanical and chemical oral hygiene measures for a period of 36 hours, allowing dental plaque to build up. Fluorescence emission measurements were taken after 12 and 36 hours on each of the six maxillary anterior teeth, four times, both before and after thorough self performed tooth cleaning.

The results are tabulated below:

| Plaque Age | Tooth type | Without Plaque Range mean | With Plaque Range mean | Absolute Difference Range mean | Relative % Difference Range mean |
| --- | --- | --- | --- | --- | --- |
| 12 h | Incisivi | 5.89–7.82 | 5.48–6.63 | 0.25 to −1.19 | 4.1 to −15.2 |
| | | 6.52 | 6.12 | −0.41 | −5.6 |
| 12 h | Canini | 6.92–7.96 | 6.84–8.27 | 0.42 to −0.82 | 6.0 to −10.3 |
| | | 7.56 | 7.42 | −0.14 | −1.8 |

-continued

| Plaque Age | Tooth type | Without Plaque Range mean | With Plaque Range mean | Absolute Difference Range mean | Relative % Difference Range mean |
|---|---|---|---|---|---|
| 36 h | Incisivi | 5.66–7.41 6.23 | 4.46–6.13 4.95 | −1.06 to −1.66 −1.28 | −1.2 to −16.7 −11.5 |

These data show a measurable difference in intensity of fluorescence emission at the wavelength associated with clean dental enamel as plaque builds up. The relative difference between plaque covered and clean tooth areas shows that mature thick plaque often reduced the fluorescence intensity to a greater extent than did the thin plaque deposit formed after 12 hr.

4. "Dynamic" measurement of tooth plaque.

Using samples of natural teeth cleaned of any deposits an artificial mandible was constructed by inserting these teeth in their natural order in a wax model. This set of teeth was "scanned" using a probe 73 like a slow moving toothbrush. In this way, i.e. the method described above with respect to FIG. 9, fluorescence intensity against time/distance across the set of teeth were obtained showing a high signal when contacting the teeth and fluorescence gaps (low signals) in the interdental regions between the teeth, these gaps being ignored.

It was found in this experiment that reproducible curves could be obtained, the fluorescence peaks of similar teeth (e.g. pre molars, molars etc) were at a similar level, it was possible to differentiate between dental enamel and interdental areas. The fluorescence signals were lower whilst scanning the sides of the teeth than the signals received by scanning the area adjacent to the gingival margin, representing the natural gradient of intensity of clean tooth surfaces.

As a consequence of these in vitro successes, in vivo tests were carried out on three volunteers who refrained from all oral hygiene for a period of 2 days. Tests as outlined above were conducted: before and after meticulous self performed tooth cleaning, over the incisal area of the teeth e.g. well as parallel to the gingival margins, and in maximilla (upper jaw) as well as mandibula (lower jaw).

Figure 11:
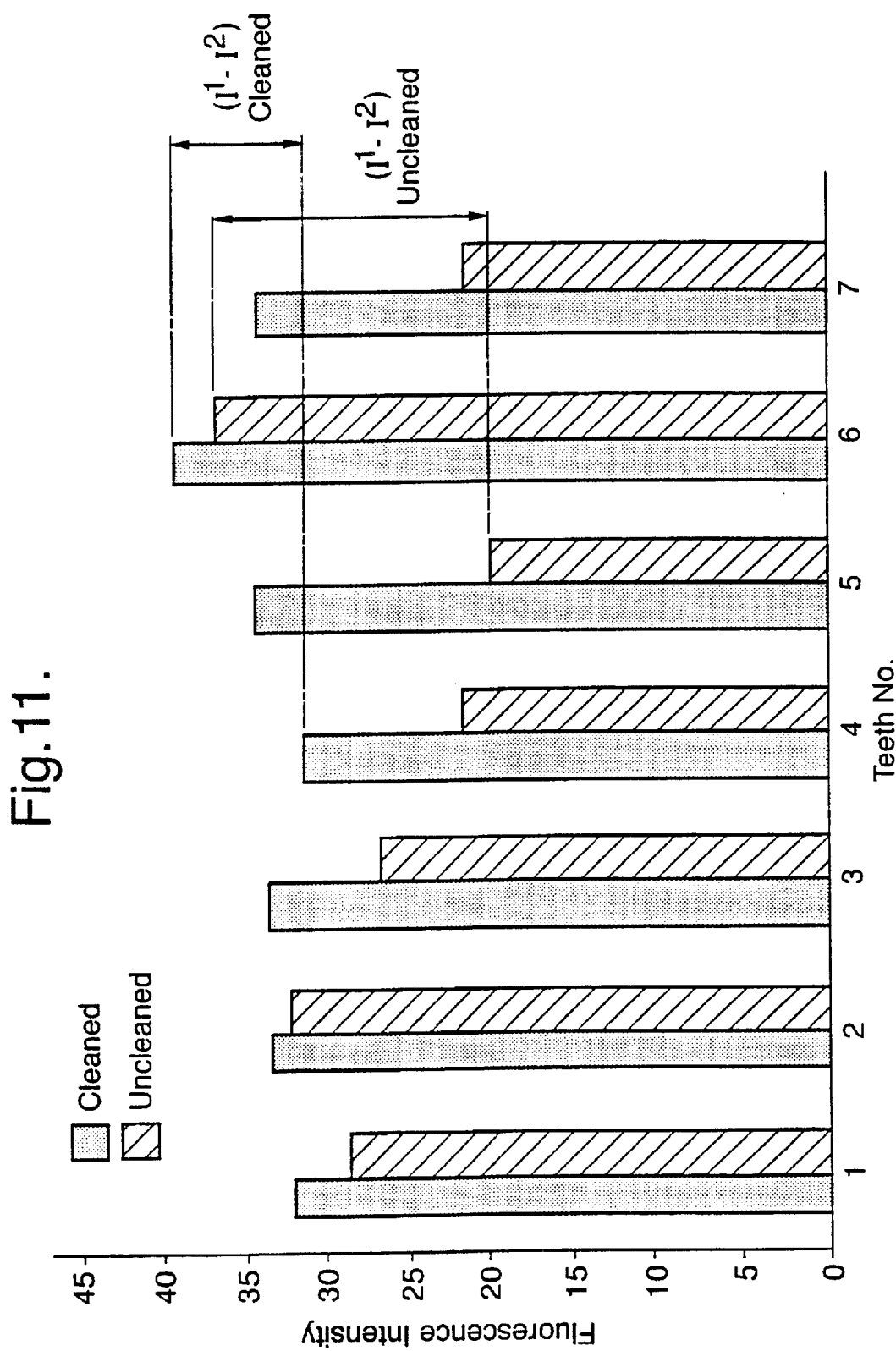
FIGS. 11 and 12 show graphs of fluorescence emission intensity from a series of teeth.
Figure 12:
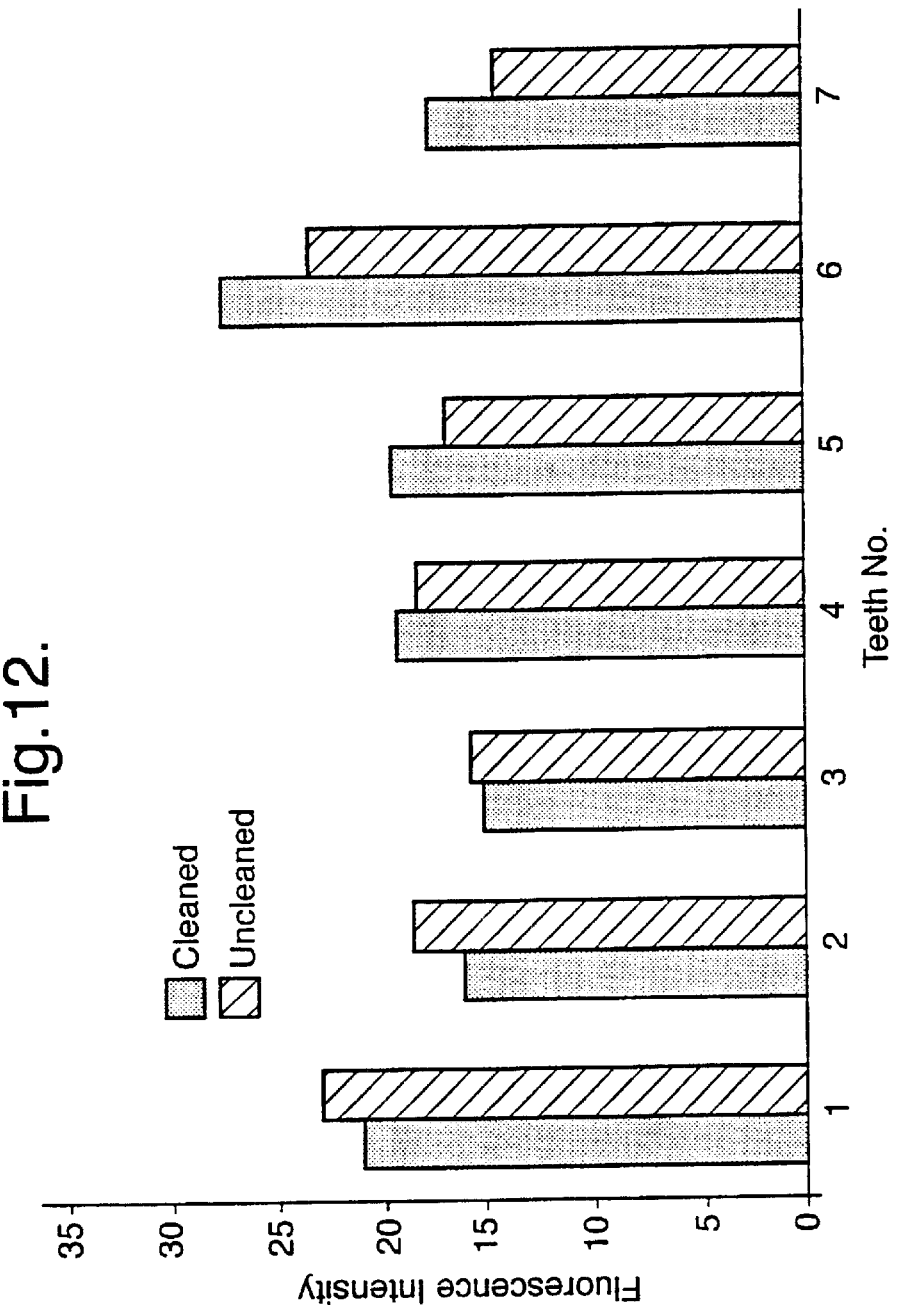

The results are indicated in FIGS. 11 and 12, which show the fluorescence emission intensity of plaque covered teeth and the same teeth after cleaning, FIG. 11 showing the measurements taken near the base of the teeth where plaque deposits form, and FIG. 12 showing measurements at the crown of the teeth where plaque deposits are very unlikely to form.

These results show that the fluorescence intensity of the clean teeth in vivo was higher adjacent to the gingiva (see FIG. 11) and lower in the incisal areas (see FIG. 12). Where little plaque is expected, i.e. in the incisi the mean values of intensity from plaque covered and clean teeth were nearly the same, see FIG. 11. Where plaque deposition is to be expected, i.e. at the gingival margin, the signals were reduced relative to the clean teeth, see FIG. 12.

For each of the teeth scanned by the moving probe it is seen that the intensity of fluorescence emission increases as the tooth is cleaned of its deposits, the increase being greater for the tooth region adjacent to the gingiva as shown in FIG. 11. Referring to FIG. 11, before cleaning the teeth, i.e. so that deposits are present, the difference in fluorescence intensity $(I^1-I^2)_{unclean}$, between the highest and lowest peaks (ignoring the "false" minima between the teeth) is ca. 17.5 intensity units. After cleaning the teeth, so that deposits are removed the difference in fluorescence intensity $(I^1-I^2)_{cleaned}$ between the highest and lowest peaks (again ignoring the "false" minima between the teeth) is reduced to ca. 8.0 intensity units, i.e. a ca. 50% reduction. Also the mean of the peak heights can be seen from FIG. 11 to have risen by ca. 20–30% as a result of cleaning the teeth. Similar results are obtained for the incisal region as shown in FIG. 12, although the difference between $(I^1-I^2)_{uncleaned}$ and $(I^1-I^2)_{uncleaned}$ and the rise in the mean is less than for the gingival region. This data shows the feasibilty of the dynamic measurements to give an indication of the presence of deposits.

5. Fluorescence measurement of single teeth

Experiments were carried out to determine whether the auto fluorescence of "clean" tooth enamel varied from position to position at different sites on surface locations along the vertical axis of the tooth, i.e. from the cervical area where the tooth meets the gumline (or gingival margin) to the incisal aspect (or crown) of the tooth. These experiments were carried out on plaque-covered as well as clean tooth surfaces. Three volunteers refrained for 2 days from any mechanical or chemical oral hygiene. These three volunteers were known to be light, average and heavy plaque producers respectively. Thereafter the enamel fluorescence of different tooth types was recorded at a maximum of 4 locations along the vertical axis, i.e. at the cervical area, the crown and two intermediate locations (1 lower, 2 higher) before and after professional tooth cleaning.

The results for a typical volunteer being a heavy plaque producer are given in the table below.

|  | Cervical | | Intermediate 1 → | | Intermediate 2 → | | Incisal | |
|---|---|---|---|---|---|---|---|---|
| Tooth | Without With Plaque | Difference In [%] | Without With Plaque | Difference in [%] | Without With Plaque | Difference In [%] | Without With Plaque | Difference In [%] |
| Upper Jaw | | | | | | | | |
| 11 | 35.5 | | 22.5 | | 25.0 | | 26.0 | |
|  | 36.5 | +2.7 | 22.0 | −2.3 | 22.5 | −11.1 | 23.0 | 13.0 |
| 23 | 57.0 | | 41.0 | | 23.0 | | 22.0 | |
|  | 45.0 | | 34.0 | −20.6 | 22.0 | −4.5 | 20.0 | −10 |

-continued

| | Cervical | | Intermediate 1 → | | Intermediate 2 → | | Incisal | |
|---|---|---|---|---|---|---|---|---|
| Tooth | Without With Plaque | Difference In [%] | Without With Plaque | Difference in [%] | Without With Plaque | Difference In [%] | Without With Plaque | Difference In [%] |
| 25 | 69.0 | | 52.0 | | 31.0 | | 23.0 | |
| | 62.0 | −11.3 | 40.0 | −30.0 | 29.0 | −6.9 | 20.5 | −12.2 |
| 26** | 86.0 | | 55.0 | | ** | | 26.0 | |
| | 54.0 | −59.3 | 32.0 | −71.9 | | | 23.5 | −10.6 |
| Lower Jaw | | | | | | | | |
| 31 | 33.0 | | 25.0 | | 25.0 | | 29.0 | |
| | 30.0 | −10 | 24.0 | −4.2 | 26.0 | +3.1 | 28.0 | −3.6 |
| 33 | 79.0* | | 63.0 | | 29.0 | | 23.5 | |
| | 71.0* | −11.3 | 49.0 | 28.6 | 24.0 | −20.8 | 21.5 | −9.3 |
| 35 | 60.0 | | 42.0 | | 29.0 | | 23.5 | |
| | 59.0 | −1.7 | 35.0 | −20.0 | 30.0 | +3.3 | 21.5 | −9.3 |
| 36** | 73.0 | | 50.0 | | ** | | 23.5 | |
| | 60.0 | −21.7 | 31.0 | −61.3 | | ** | | +16.1 |

*Dentino—Enamel junction
**Only 2 values available

The results for the three volunteers are summarised in the table below, which shows the change in fluorescence emission intensity on removal of the plaque deposits.

| | | Change in fluorescence intensity | | | |
|---|---|---|---|---|---|
| Volunteer | Plaque | Cervical | Median | Incisal | Median |
| 1 | light | 4.8 to −61.0 | −1.8 | 9.6 to −8.6 | ±0 |
| 2 | average | 7.2 to −26.3 | −8.7 | 5.6 to −9.4 | ±1.0 |
| 3 | heavy | 2.7 to −59.3 | −11.3 | 16.1 to −13.0 | −9.7 |

The results show that there is a gradient of auto fluorescence intensity with distance along the tooth with distance along the tooth vertical axis, starting with high fluorescence intensities at the gingival margin (cervical) to lower and more evenly distributed intensities of the incisal aspect (crown). Especially high values were obtained when the so-called dentino-enamel junction was accessible to the probe.

Fluorescence emission intensity was reduced by plaque deposits to a greater or lesser extent related to plaque thickness and location. At the incisal aspect no plaque was expected, and with all the volunteers, although variation in intensity of the fluorescence emission was found, the median value of the change in intensity on plaque removal was 1 to 0 for light and average plaque formation and ca. 10% for heavy plaque formation. In contrast, in the cervical area where the most plaque was to be expected the reduction of the fluorescence intensity was greatest, e.g. ca. 11% being recorded for heavy plaque formation.

Figure 13:
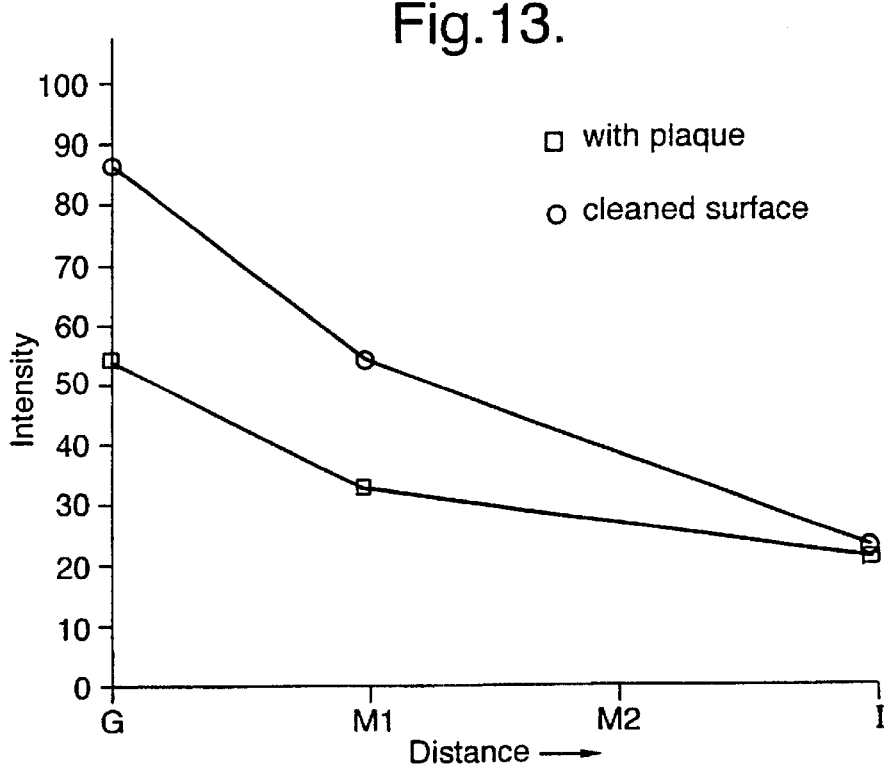
FIG. 13 shows a graph of fluorescence intensity with distance along the tooth vertical axis.

These results can be expressed as the graph shown in FIG. 13, which shows the variation in intensity of fluorescence emission at a wavelength corresponding to emission from clean tooth surfaces with vertical distance up the tooth, both for a clean surface and with the presence of plaque deposits. By this graph it can be seen that for two points separated along the vertical tooth axis from the gingival margin to the incisal aspect there is a steeper gradient in the intensity of fluorescence emission from a tooth with plaque deposits on its surface than for a clean tooth. Measurement of this gradient may be used as the basis for detection of dental plaque on the tooth surface, and a change to a less steep gradient during tooth cleaning may associated with an initial presence followed by subsequent removal, of plaque.

What is claimed is:

1. An apparatus for detecting biological deposits on the surface of a tooth which comprises:
   illumination means to direct exciting radiation at a wavelength up to 530 nm onto a test tooth surface believed to have a biological deposit thereon,
   detection means to detect fluorescence radiation, at a wavelength associated with that of auto fluorescence emission from a substantially biological deposit-free tooth surface, emitted from the test tooth surface in response to the exciting radiation,
   conversion means to convert the fluorescence radiation into an electrical signal,
   electronic data processing means to process the electrical signal and to associate the electrical signal with the presence of biological deposits on the test tooth surface, and to make a comparison of the intensity of the said fluorescence emission from the test tooth surface with an intensity of auto fluorescence emission, at a wavelength associated with that of auto fluorescence emission from a substantially biological deposit-free tooth surface, from a tooth surface believed to have less biological deposit thereon than is believed to be present at the test tooth surface, and to associate a reduction in intensity of the auto fluorescence relative to the intensity of auto fluorescence from a tooth surface known to have less biological deposit thereon than is present on the test tooth surface with the presence of biological deposits on the test tooth surface, and,
   indicator means to indicate the presence of such biological deposits to a user of the device.

2. An apparatus according to claim 1 wherein the illumination means emits exciting radiation which has a wavelength 420–530 nm.

3. An apparatus according to claim 2 wherein the detection means detects the fluorescence emission over a wavelength range above 520 nm.

4. An apparatus according to claim 1 wherein the detection means detects the fluorescence emission over a wavelength range above 520 nm.

5. An apparatus according to claim 4 wherein the intensity of auto fluorescence emission from biological deposit-free or substantially biological deposit-free tooth surfaces is stored as a reference standard in the device.

6. An apparatus according to claim 1 wherein the intensity of auto fluorescence emission from biological deposit-free or substantially biological deposit-free tooth surfaces is stored as a reference standard in the device.

7. An apparatus according to claim 6 constructed to initially measure the intensity of auto fluorescence emission from the tooth surface believed to have less biological deposit thereon than is believed to be present at the test tooth surface, and to use the intensity as a basis for the comparison with the intensity of emission from the test tooth surface.

8. An apparatus according to claim 1 constructed to initially measure the intensity of auto fluorescence emission from the tooth surface believed to have less biological deposit thereon than is believed to be present at the test tooth surface, and to use the intensity as a basis for the comparison with the intensity of emission from the test tooth surface.

9. An apparatus according to claim 8 wherein the detection means is moveable between spaced apart locations on the user's teeth, so that in the course of this movement the exciting radiation is directed onto a plurality of spaced apart tooth surfaces on the same or different teeth, the variation of fluorescence emission detected as the device moves around the user's mouth is measured, and wherein the measurement thus obtained is associated with the presence of biological deposits on the test tooth surface.

10. An apparatus according to claim 1 wherein the detection means is moveable between spaced apart locations on the user's teeth, so that in the course of this movement the exciting radiation is directed onto a plurality of spaced apart tooth surfaces on the same or different teeth, the variation of fluorescence emission detected as the device moves around the user's mouth is measured, and wherein the measurement thus obtained is associated with the presence of biological deposits on the test tooth surface.

11. An apparatus according to claim 10 wherein the device is adapted to measure the difference between highest and lowest intensities of fluorescence emission and to associate changes in this difference during a process of tooth cleaning with the presence of biological deposits on the test tooth surface.

12. An apparatus according to claim 11 wherein the device is adapted to measure the mean between highest and lowest intensities of fluorescence emission and to associate an increase in this mean during a process of tooth cleaning with the presence of biological deposits on the test tooth surface.

13. An apparatus according to claim 11 constructed to ignore any fluorescence intensify below a specified certain minimum value.

14. An apparatus according to claim 10 wherein the device is adapted to measure the mean between highest and lowest intensities of fluorescence emission and to associate an increase in this mean during a process of tooth cleaning with the presence of biological deposits on the test tooth surface.

15. An apparatus according to claim 14 wherein;
the detection means is adapted to detect a fluorescence emission during a period of time over which the detection means moves from one tooth area to one or more other tooth areas;
detect maxima in the emission intensity with time;
and to measure and compare the heights of such maxima.

16. An apparatus according to claim 10 constructed to ignore any fluorescence intensity below a specified certain minimum value.

17. An apparatus according to claim 1 wherein;
the detection means is adapted to detect a fluorescence emission during a period of time over which the detection means moves from one tooth area to one or more other tooth areas;
detect maxima in the emission intensity with time;
and to measure and compare the heights of such maxima.

18. An apparatus according to claim 17 wherein the electronic data processing means measures the difference between the height of the lowest and the highest peaks of fluorescence emission intensity and associates this difference with the presence of biological deposits which are then indicated to the user.

19. An apparatus according to claim 18 wherein the detection means detects fluorescence emission from two spaced apart regions of tooth surface, and compares the relative intensities of fluorescence emission from these two spaced apart surfaces, to associate any difference between the relative intensities with the presence of biological deposits on the tooth surface and to indicate the presence of such deposits to the user.

20. An apparatus according to claim 1 wherein the detection means detects fluorescence emission from two spaced apart regions of tooth surface, and compares the relative intensities of fluorescence emission from these two spaced apart surfaces, to associate any difference between the relative intensities with the presence of biological deposits on the tooth surface and to indicate the presence of such deposits to the user.

21. An apparatus according to claim 20 having two detection means positioned relative to each other so that when the device is inserted into the mouth one of the two detection means is likely to be positioned adjacent a tooth at or near the gumline and the other at or near the crown of the tooth.

22. An apparatus according to claim 21 comprising a toothbrush head with two detection means positioned across the width of the toothbrush.

23. An apparatus according to claim 1 wherein the electronic data processing means detects the presence of or measures any gradient in fluorescence emission intensity with distance across a test tooth surface as the device moves from one part of a tooth surface to another.

24. An apparatus according to claim 23 wherein the electronic data processing means detects or measures changes in the gradient during a process of tooth cleaning.

25. An apparatus according to claim 18 wherein the apparatus additionally comprises;
detection means to detect auto fluorescence emission from the test tooth surface at a wavelength associated with auto fluorescence emission from biological deposits on a tooth surface, and
means to relate this auto fluorescence emission to the presence of biological deposit on the test tooth surface, and
indicator means to indicate the presence of biological deposit to a user of the device.

26. An apparatus according to claim 1 wherein the apparatus additionally comprises;
detection means to detect auto fluorescence emission from the test tooth surface at a wavelength associated with auto fluorescence emission from biological deposits on a tooth surface, and
means to relate this auto fluorescence emission to the presence of biological deposit on the test tooth surface, and
indicator means to indicate the presence of biological deposit to a user of the device.

27. An apparatus according to claim 26 wherein the detection means is capable of detecting auto fluorescence emission from the test tooth surface at a wavelength associated with auto fluorescence emission from dental plaque on the tooth surface.

28. An apparatus according to claim 27 wherein the detection means detects exciting radiation at a wavelength 470±40 nm.

29. An apparatus according to claim 1 wherein the detection means detects exciting radiation at a wavelength 470±40 nm.

30. An apparatus according to claim 29 wherein the illumination means comprises a light guide comprising one or more optical fibres for directing the exciting radiation onto a test tooth surface, and the detector means comprises a light guide comprising one or more optical fibres to guide fluorescence emission from the tooth surface to a detector for the fluorescence emission radiation.

31. An apparatus according to claim 1 wherein the illumination means comprises a light guide comprising one or more optical fibres for directing the exciting radiation onto a test tooth surface, and the detector means comprises a light guide comprising one or more optical fibres to guide fluorescence emission from the tooth surface to a detector for the fluorescence emission radiation.

32. An apparatus according to claim 31 wherein the optical fibres comprising the light guide of the illumination means and the detection means are bundled together within a conduit and terminate at a common optical probe.

33. An apparatus according to claim 32 wherein a greater number of fibres is used for the light guide of the emission radiation than for the excitation radiation.

34. An apparatus according to claim 31 wherein a greater number of fibres is used for the light guide of the emission radiation than for the excitation radiation.

35. An apparatus according to claim 34 having a cut-off filter to prevent radiation with a wavelength below ca 420 nm from reaching the tissues of the user.

36. An apparatus according to claim 1 having a cut-off filter to prevent radiation with a wavelength below ca 420 nm from reaching the tissues of the user.

37. An apparatus according to claim 36 wherein the cut-off filter is a dichroic mirror filter.

38. An apparatus according to claim 1 wherein the excitation radiation and the detection of the fluorescent emission are modulated or phase locked.

39. An apparatus according to claim 37 wherein the excitation radiation and the detection of the fluorescent emission are modulated or phase locked.

40. An apparatus according to claim 39 which comprises a toothbrush having a toothbrush head and having the illumination means and the detection means incorporated into the toothbrush head.

41. An apparatus according to claim 1 which comprises a toothbrush having a toothbrush head and having the illumination means and the detection means incorporated into the toothbrush head.

42. An apparatus according to claim 41 wherein the indicator means indicates the initial presence of biological deposits on the surface of the user's teeth and indicates the quantitative reduction or absence of biological deposits after the teeth have been brushed for a period of time.

43. An apparatus according to claim 42 wherein the indicator means indicates to the user that biological deposits are present somewhere in an area of the user's teeth, and that continued brushing of the teeth is necessary to remove the deposits.

44. An apparatus according to claim 41 wherein the indicator means indicates to the user that biological deposits are present somewhere in an area of the user's teeth, and that continued brushing of the teeth is necessary to remove the deposits.

* * * * *